United States Patent [19]
Lindow

[11] Patent Number: 4,877,438
[45] Date of Patent: Oct. 31, 1989

[54] MICROBIAL AND CHEMICAL CONTROL OF FRUIT RUSSETTING

[75] Inventor: Steven E. Lindow, Berkeley, Calif.

[73] Assignee: The Regents of the University of California, Berkeley, Calif.

[21] Appl. No.: 80,707

[22] Filed: Aug. 3, 1987

[51] Int. Cl.[4] ...................... A01N 63/00; A01N 25/00
[52] U.S. Cl. ........................................... 71/79; 424/93
[58] Field of Search ................... 424/93; 426/270, 321, 426/331; 71/79; 47/1 R

[56] References Cited

U.S. PATENT DOCUMENTS

| | | | |
|---|---|---|---|
| 2,284,970 | 6/1942 | Avery, Jr. | 71/96 |
| 4,061,488 | 12/1977 | Mann | 424/93 |
| 4,476,110 | 10/1984 | Heye et al. | 424/93 |
| 4,519,163 | 5/1985 | Bonner | 47/DIG. 9 |
| 4,582,704 | 4/1986 | Baker et al. | 424/93 |
| 4,764,371 | 8/1988 | Pusey et al. | 424/93 |
| 4,798,723 | 1/1989 | Dart et al. | 424/93 |

FOREIGN PATENT DOCUMENTS 0210734  2/1987  European Pat. Off. ............. 424/93

OTHER PUBLICATIONS

Saltviet, "Effects of Calcium and Auxin on Russet Spotting...", BA 83:13245.
Lynch, "Plant Growth Regulators", taken from CRC Handbook of Microbiology, 2nd Edition, vol. VI, p. 289.
Walter, Ann. Rpt. East Mailing Res. Sta. for 1966, pp. 83–95.
Faust & Shear, Hort. Science, (1972), 7:233–235.
DeVries, Acta. Bot. Neerl., (1968), 17:405–415.
Kenneth V. Thimann & A. Carl Leopold, in *The Hormones*, Pincus and Thimann, Eds., Academic Press, New York, (1955), 3:1–56.
Robert S. Bandurski & Heather M. Nonhebel, in *Advanced Plant Physiology*, Wilkins, Ed., Pitman Publishing, Marshfield, Mass., (1984), pp. 1–20.

Primary Examiner—Glennon H. Hollrah
Assistant Examiner—K. L. Konstas
Attorney, Agent, or Firm—Richard L. Neeley

[57] ABSTRACT

A method is provided of reducing fruit russetting by treating the surface of a fruit to reduce the amount of auxins present on the surface. In a preferred embodiment, the population of auxin-producing bacteria is reduced by providing a competing auxin-deficient bacterial population.

6 Claims, No Drawings

MICROBIAL AND CHEMICAL CONTROL OF FRUIT RUSSETTING

TECHNICAL FIELD

This invention is related to techniques for improving fruit storage and appearance and is particularly directed to preventing russetting of fruit.

BACKGROUND

The preferred appearance of most fruit varieties is a clear, smooth surface. Fruit with imperfections or blemishes on the fruit surfaces known as russetting are generally considered inferior by consumers. Accordingly, such fruit brings a considerably lower price to producers. Additionally, russetted fruits also are not as amenable to long-term storage as fruit without such imperfections. Thus, fruit russetting is one of the major horiticultural problems associated with the production of various fruits.

Because of the importance of fruit russetting to crops such as pears and apples, there is a considerable body of world-wide literature on this phenomenon. Most of the references are either etiological or are rather anecdotal. For example, considerable attention has been given to the development of fruits, particularly the epidermal cell layers, during the growth process. There is a general understanding that cracks in the cuticle layer of the fruit surface and/or the death of individual epidermal cells by different causes stimulate the production of cells containing considerable amount of cutin and cork. Such dead cells lead to the rough, browned appearance that is typical of russetting.

One major school of thought has been that russetting is induced in the earliest stages of fruit development (from 1-4 weeks after the flowers fall from the trees). During this time the surface area of the fruit is expanding most rapidly (from a relative view point). The stretching of the epidermal cells to cause breaks in the cuticle and/or death in the cells has been considered one cause of fruit russetting. Additionally, fruit russetting has been associated with various environmental and chemical causes, such as cool, moist weather and orientation of the growing fruit to the environment. Fruit russetting has been examined almost exclusively by plant physiologists, botanists, and horticulturists from the standpoint of the response of the developing fruit to its physical and environmental surroundings.

Efforts to reduce fruit russetting have generally been ineffective. Recent experimental applications of gibberellic acid have shown some promise but have been sporadic in their results and have caused undesirable changes in the fruit morphology and/or other detrimental effects on plant growth. Accordingly, there remains considerable need for improved techniques for reducing fruit russetting.

RELEVANT LITERATURE

Walter, *Ann. Rpt. East Malling Res. Sta.* for 1966:83–95, reviews russetting and cracking in apples. Faust and Shear, Hort. Science (1972) 7:233–235 provides an interpretive review of russetting of apples. Both of these articles list numerous publications dealing with fruit russetting. De Vries, *Acta. Bot. Neerl.* (1968) 17:405–415, describes the development of the structure of russetted apple skin.

SUMMARY OF THE INVENTION

The present invention provides a method of reducing fruit russetting by identifying a cause of russetting and providing techniques to counteract this cause. Russetting has been demonstrated to occur in the presence of auxin-producing bacteria on the surface of fruit. Specific techniques of the invention therefore either act directly on auxin-produced russetting by eliminating auxing from fruit surfaces or act indirectly on auxin production by reducing the population of auxin-producing bacteria, either by killing such bacteria or by providing a bacterial population that does not produce auxins but which successfully competes with auxin-producing bacteria for surface space, or by removing auxin precursors, such as tryptophan, from the surface of the fruit. Thus, by having discovered that russetting is a problem of bacterial infection on fruit surfaces, the present inventor provides a number of ways of reducing russetting by either reducing the population of auxin-producing bacteria or the auxins produced by such bacteria.

DETAILED DESCRIPTION OF SPECIFIC EMBODIMENTS

The present invention arose out of discoveries that fruit russetting is associated with the presence of various bacteria that colonize fruit surfaces and produced auxins. The term auxin encompasses a number of compounds having common biological characteristics in plants. These are typically stimulation of cell division, stimulation of shoot growth, control of vascular system differentiation, control of tissue culture differentiation, control of apical dominance, delay of senescence, promotion of flowering and fruit setting, and ripening. The prototypical auxin is indole-3-acetic acid (IAA), whose structure is shown below:

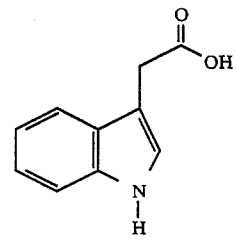

Other known, naturally occurring auxins include phenylacetic acid and 4-chloroindole-3-acetic acid. Although there are some exceptions, the major requisites for biological activity appear to be an aromatic ring and a carboxyl group at least one carbon removed from the ring. Typically a free ortho position or a strong electron-withdrawing substituent is present. Thimann and Leopold, in *The Hormones*, Pincus and Thimann, Eds., Academic Press, New York (1955) 3:1–56, describe a charge-separation theory indicating that there must be a negative charge on the carboxyl and a positive charge on the ring system which must be about 5.5 Å(0.55 nm) from the negative charge. Auxins and their normal biological roles are discussed in Bandurski and Nonhebel, in *Advanced Plant Physiology*, Wilkins, Ed., Pitman Publishing, Marshfield, Mass. (1984), pp. 1–20.

Russetting occurs at least in part as a result of auxin-producing bacteria, particularly bacteria that produce indole-3-acetic acid, being present on the surface of fruit. It has not been firmly established that this is the only cause. Nevertheless, the amount of russeting is reduced by reducing the effects of exogenous auxins on the fruit surface, as shown by the examples which are set forth below. It is also possible to reduce the amount of auxins by eliminating from fruit surfaces tryptophan and other precursors in the biochemical synthesis of IAA. Accordingly, fruit russeting can be reduced by any of several techniques: (1) reducing the population of auxin-producing bacteria on fruit surfaces, (2) reducing the amount of auxin present on fruit surfaces after it has been produced by bacteria, and (3) reducing the production of auxins by bacteria. Chemical, biochemical, and biological methods can be used for all of these techniques.

The first general technique is to reduce the population of auxin-producing bacteria on the surface of fruit. A preferred technique used to achieve this result is to provide for the establishment of auxin-production-deficient microorganisms capable of growing on the fruit surface. The deficient microorganisms are selected from native, mutagenized, or genetically engineered microorganisms by any method that establishes their ability to colonize the surface of the fruit being protected. It is recognized that different microorganisms may be selected for different fruits. Although it is desirable to have an auxin-deficient microorganism having superior growth characteristics that will enhance its ability to compete with auxinproducing microorganism, enhanced growth characteristics are not required if the auxin-deficient microorganism is applied to the fruit surface and colonizes the surface at an early time since competition for nutrients present on the fruit surface will tend to inhibit later colonization by an auxin-producing species.

The auxin-deficient microorganisms may be obtained from endogenous microorganisms of the plant, mutagenized organisms, or genetically engineered organisms. The microorganisms or bacteria can be any microorganism which populates fruit surfaces and which increase in population during fruit development. In view of the wide variety of species and strains that can be employed, no single species can be indicated as the sole species to be used. Of particular interest are species and strains of Pseudomonas, Erwinia, Corynebacterium, Xanthomonas, and Bacillus. The auxindeficient organisms are selected by any convenient means that distinguishes between auxin-producing and auxin-deficient microorganisms. A number of biological assays for detecting the presence of auxins are described in the Bandurski and Nonhebel publication cited above and/or publications cited therein. A typical selection technique is using a colorometric reaction is based on a combination of the Van Urk and Salkowski reagent as described by Ehmann. The color reaction is described in Percival and Bandurski, *Plant Physiol.* (1976) 58:60-67. To a sample (containing microorganisms or a microorganism supernatant) suspected of containing IAA in a volume of 50 $\mu$l of 50% ethanol is added a reagent consisting of one part Salkowski reagent and one part Ehrlich reagent. After heating at 45° C. for 30 min, a stable color develops. The sample is diluted to 1 ml with 50% ethanol and can be estimated quantitatively at 615 nm against an appropriate blank. A full scan of the color present in the sample detects interfering compounds. The method can be scaled down, and sensitivities to a fraction of a microgram are possible. Such colorometric assays are generally more convenient than biological assays, such as the Avena curvature test or the Avena straight growth assay, which are described in the Bandurski and Nonhebel publication. If desired, tests for biological activity can be combined with colorometric assays to confirm the absence of auxins.

Once an organism has been selected for its property of being auxin-deficient, its ability to colonize fruit surfaces should be verified. Even if the auxin-deficient microorganism is selected from microorganisms that normally colonize fruit surfaces, the verification ensures that the selection process for an auxin-deficient microorganism did not select a mutant or contaminating organism incapable of colonizing the fruit surface. Ability to colonize fruit can be established by spraying formulations of the microorganism (see below) onto developing fruit followed by re-isolation of the organism from the fruit surface.

Microorganisms having superior competitive growth characteristics can be selected by initially spotting the microorganisms onto the surface of a defined medium encompassing the relative proportion of limited nutrients normally available on the fruit surface. By limited is intended that the amount available limits the overall cell population on the surface. The medium normally includes a mixture of sugars and amino acids, particularly the dicarboxylic amino acids and their monoamides, which appear to be utilized by microflora on the host fruit surface and is in limited availability to the microflora. Normally, one or more uronic acid or inorganic salt will also be included. These are incorporated into an appropriate medium substrate, such as agar. Of the active ingredients, sugars will generally be present in the range of about 80-95 weight percent, while the total amino acids and the total inorganic salts will each be present in the range of about 2-10 weight percent. The total amount of nutrients will generally be about 0.01 to 2, usually about 0.1 to 1, weight percent of medium substrate.

The medium employed supports a limited growth of most randomly selected fruit-surface bacteria. Bacteria which grow on this nutrient medium deplete the medium of selected nutrients in a zone around their area of growth. The randomly spotted auxin-deficient microorganisms which deplete nutrients which are critical for the survival and growth of auxin-producing bacteria can be selected by growing the bacteria on the nutrient medium surface to establish colonies and deplete the nutrient source.

The surface supporting the colonies is then oversprayed with a suspension of auxin-producing cells, which can be selected by the same procedures as described above for selecting auxin-deficient microorganisms, but selecting for the presence of auxins rather than their absence. Such auxin-producing bacteria can readily be isolated from the fruit of orchards that are subject to severe russeting problems. The auxin-producing bacteria atomized over the surface of the plate will grow in the areas in between the spotted areas containing antagonistic auxin-deficient bacteria. The antagonistic bacteria are indicated by a clear zone resulting from no growth of the applied auxin-producing bacteria surrounding the patch area on the surface of the nutrient surface spotted with the antagonistic auxin-deficient bacteria.

Although the techniques set forth above for identifying competitive colonies through laboratory testing are sufficient to identify useful microorganisms, it must be recognized that there are significant differences between field conditions and laboratory conditions. Accordingly, it is preferred to isolated the auxin-deficient microorganisms from orchards where the microorganisms are subject to field conditions and to confirm any laboratory results with field testing using the techniques described below for innoculating fruit with the various bacteria.

The auxin-deficient microorganisms can be modified in accordance with conventional techniques to induce novel genetic capabilities. These techniques, for the most part, involve transformation, transduction, and conjugation. Various genetic capabilities which can provide advantages for the auxin-deficient microorganism include imparting antibiotic resistance, bacteriocin production, improved growth characteristics, or the like. By providing for a marker which allows for selection of transformants or conjugants, the desired organisms can be readily selected. Markers include antibiotic resistance, colacin resistance, heavy metal resistance, prototrophy (in an auxotropic host), or the like.

The subject microorganisms can be employed with a wide variety of crop plants, especially pome and stone fruits. Examples include pears, apples, peaches, apricots, and plums.

Depending on the nature of the plant and the microorganism being used, a variety of methods and compositions can be employed for application of the competitive organism to the plant. In addition, it may be desirable to use mixtures of organisms or to carry out multiple treatments.

The number of cells per unit formulation will depend upon whether the formulation is intended to be used in a dry or wet state. For wet formulations (e.g., fruit sprays, suspensions, aerosols, mists, and the like), the number of cells per ml will generally be from about $10^5$ to $10^{10}$ cells/ml. Generally, it is desired to have about $10^4$ to $10^{10}$ cells/gram fr. wt. (fresh weight) of material being sprayed. For dry formulations, the number of cells will generally range from about $10^4$ to $10^9$ cells/gram of formulated product. Sprays of antagonistic auxin-deficient microorganisms are generally most effective when sprayed onto flowering fruit trees at a phenological stage of approximately 80% bloom. When applied at this percentage bloom, most flowers are open, and the developing fruit (pistles) are as yet uncolonized by auxin-producing bacteria and are suitable for colonization by the applied auxin-deficient bacteria. One additional application of a similar concentration of cells at about 10 days after petal fall should ensure adequate colonization of young developing fruit for russet control. Under severe weather conditions, additional applications may be required. Bacteria can be applied with standard spray equipment, such as orchard sprayers, using standard agricultural practices.

In aqueous formulations various additives may be included in minor amounts. Additives include surfactants, dyes, nutrients, buffers, biological or chemical pesticides used at similar times (such as herbicides and pesticides), and like. In dry formulations, additives include inert powders, bacterial stabilizing agents, salts, anticaking agents, nutrients, buffers, film-forming materials, biological or chemical pesticides, and the like. The various additives will range in concentration from about $1 \times 10^{-4}$ to 1% by weight with the exception of herbicides and pesticides. If a combined formulation intended for use both as a herbicide or pesticide and as an anti-russetting composition, it will contain the normal amounts of the two or more active ingredients. Other additives may be included for specific situations.

A number of compositions and techniques for applying bacterial suspensions and other compositions containing microorganisms to plants are described in U.S. Pat. No. 4,432,160, which describes the use of microorganisms to inhibit frost damage to plants.

Chemical and biochemical techniques can also be used to reduce the population of auxin-producing bacteria on fruit surfaces. There is no distinct border between such chemical and biochemical techniques. Biochemical techniques are generally associated with the use of some biochemical substance in a cell-free composition. The prase "biochemical substance" is intended to encompass compounds of biological origin that are difficult to produce chemically and includes material such as enzymes and complex growth regulators. The phrase "chemical materials" is intended to cover molecules readily produced by synthetic techniques. Since modern synthetic organic chemistry is capable of producing numerous large molecules (and in order to avoid complex wording), use of materials of biological origin and/or chemical origin in a cell-free environment is covered by the phrase "cell-free treatment".

Cell-free treatments include techniques that will reduce the population of auxin-producing bacteria on the surface of fruit. Such techniques include the use of antibiotics and bacteriostatics. Although an antibiotic or bacteriostatic that is selective for an auxin-producing bacterium is preferred, such selection is not required since reducing the entire population of bacteria on the fruit surface will be effective to reduce the amount of auxin present. However, the widespead use of antibiotics and bacteristatics in the environment is not desirable because of the likelihood of developing resistant strains and is further likely to be more expensive than biological control.

Additionally, use of biochemical or chemical techniques to reduce the population of bacteria on a fruit surface is likely to be ineffective for long-term treatment, unless a persistent antibiotic is used. If a rapidly degrading antibiotic is applied to fruit, auxin-producing bacteria in the environment will repopulate the fruit surface after the antibiotic has degraded. However, use of chemical and/or biological methods to initially reduce the population of auxin-producing bacteria to allow establishment of an auxin-deficient bacterium is a preferred manner of treatment, particularly if a selective antibiotic is used. As described above, specific antibiotic resistance can be engineered into a particular auxin-deficient bacterial strain intended for use with the method of the present invention.

Another means of attacking the russetting problem is to reduce the amount of auxin produced by the bacterial population on the fruit surface. One manner of accomplishing this result is to decrease the amount of available precursor. The principal normal precursor for IAA and similar auxins is tryptophan. Accordingly, any method of reducing the amount of tryptophan available should also reduce russetting. Tryptophan-degrading bacteria have been established on pear fruit in trials. The use of such microorganisms or of enzymes from such microorganisms to reduce the amount of available tryptophan would therefore be within the scope of the present invention. Microorganisms capable of degrading tryptophan include numerous Pseudomonas, Erwinia, Corynebacterium, Xanthomonas, and Bacillus species capable of colonizing fruit surfaces. Tryptophan-degrading microorganisms can readily be recognized by their ability to grow on a medium which provides tryptophan as the sole carbon source. Microorganisms capable of metabolizing other IAA precursors by alternative pathways that do not lead to IAA can be selected in the same manner.

It is also possible to reduce fruit russetting by destroying or otherwise removing auxins present on fruit surfaces after they have been produced. For example, microorganisms have been identified that degrade indole-3-acetic acid. Either these organisms or compositions containing cell-free extracts or purified components obtained from these organisms can be used to reduce the amount indole present on the fruit surface. IAA-degrading microorganisms can readily be recognized by their ability to grow on a medium which provides IAA as the sole carbon source. Microorganisms capable of metabolizing other auxins can be selected in the same manner. The selections are typically made from the numerous Pseudomonas, Erwinia, Corynebacterium, Xanthomonas, Bacillus, and other species capable of colonizing fruit surfaces.

Biological methods of control are preferred over chemical ones for several reasons. First, there is a reduction in the environmental toxin load. Second, the presence of high levels of auxin-producing bacteria can overpower chemical methods of eliminating auxins or auxin precursors. Additionally, techniques that reduce the population of auxin-producing bacteria without providing a competing bacterial flora are often not effective for long-term russetting control since environmental bacterial will repopulate the fruit surface. Accordingly, techniques that provide for the growth of auxin-deficient microorganisms on fruit surfaces are preferred over other techniques.

The invention now being generally described, the same will be better understood by reference to the following detailed examples which are provided for purposes of illustration and are not to be considered limiting of the invention unless so specified.

EXAMPLES

EXAMPLE 1

Selection of Auxin-Deficient and Auxin-Producing Microorganisms

Microorganisms were isolated using standard bacteriological techniques from fruit surfaces and cultivated on standard growth media. The presence or absence of auxins in the culture medium was determined using Salkowski's reagent (0.01M $SeCl_3$ in 35% $HClO_4$), which forms a red chromophore with a maximum absorbance at 530 nm in the presence of indocompounds. Thirty min after addition of Salkowski's reagent to culture filtrates, color change was noted, and absorbance at 530 was recorded (Beckman Model 35 Spectrometer). The limit of indole detection was approximately 1 µg/ml by this method.

The presence of indole-3-acetic acid (IAA) was verified using a thin-layer chromatography technique. Ninety-six-hour cultures in KBM or in minimal medium with tryptophan, growing with shaking at 20° C., were adjusted to pH 3.0, extracted three times with an equal volume of ethyl acetate, evaporated to dryness in a flash evaporator, solubilized in a minimum volume of methanol, and spotted on a Whatman LK6DF silica gel thin layer chromatography plate. Plates were developed in two separate solvent systems, CEF (chloroform:ethyl acetate:formic acid; 50:40:10) or EIA (ethyl acetate: isopropanol:ammonia; 45:35:20). Plates were sprayed with Ehrlich∝s reagent (0.2% p-dimethylaminobenzaldehyde in a 1:1 mixture of 95% ethanol and concentrated HCl) immediately upon removal from the developing chamber. Detection of IAA was by observation of a blue band with an Rf corresponding to that of IAA standards. The recovery of IAA was determined by incorporation of freshly prepared IAA standards in culture medium before initiating the extraction procedure. The limit of IAA detection was below 0.10 µg/ml.

EXAMPLE 2

Affect of Auxin-Producing Bacteria on Fruit

A number of microorganism strains (both bacteria and yeast) were applied to developing pear fruit under field conditions. The control sample contained all components of the formulation other than the auxinproducing microorganism. Both auxin-producing and auxin-deficient bacteria were used. The severity of pear fruit russetting is shown in the following table:

TABLE 1

| Severity of Pear Fruit Russetting on Trees Treated with Auxin-producing Bacteria | | |
|---|---|---|
| Treatment | IAA Production | Russetted Area (%) |
| TS65 | + | 4.5 a |
| TS68 | + | 4.3 ab |
| Wasco 4 | + | 4.2 ab |
| 7SR7 | + | 3.7 bc |
| JL3072 | + | 3.5 cd |
| Pear 764* | − | 2.9 de |
| TS67 | +$^w$ | 2.8 de |
| Pear 64* | − | 2.7 ef |
| Ore Pot 1116 | − | 2.7 ef |
| TLP2* | − | 2.5 efg |
| 31-48 | − | 2.5 efgh |
| Pot 1193* | − | 2.3 fgh |
| D6 | − | 2.2 fgh |
| Pear 1016* | − | 2.2 fghi |
| YL2 | − | 2.2 fghij |
| Control | − | 2.1 ghij |
| AS17 | − | 2.0 hij |
| Cit 7* | − | 1.9 ij |

Entries under "Treatment" refer to the particular microorganisms used. YL2 is a yeast. The strains marked with an asterisk are all *Pseudomonas syringae* strains. The other strains are all oxidasepositive fluorescent pseudomonads. Under the heading, "IAA Production", +indicates formation of IAA by the corresponding strain, +$^w$ represents weak production, and—represents no detectable production of IAA. The letters following the entries under the heading, "Russetted" indicate whether a significant difference exists. Entries with the same letter do not show a significant difference.

EXAMPLE 3

Severity of Pear Fruit Russetting on Trees Treated with IAA-Producing Bacterial at Flowering In a similar experiment, compositions containing various microorganisms with or without tryptophan were sprayed on fruit trees at flowering. The results are shown in Table 2 below. The strains indicated by an asterisk are pseudomonads. The other strains were unidentified, but are probably enterics such as Enterobacter. The greatest percent russetting was seen in fruit treated with a composition containing both an IAA-producing bacterium and tryptophan, an IAA precursor. As before, treatment with IAA-producing bacteria produced fruit with a greater russetted surface than that of controls.

TABLE 2

Severity of Pear Fruit Russetting on Trees Treated with IAA-producing Bacteria at Flowering

| Treatment | IAA Production | Russetted Area (%) |
|---|---|---|
| T565* + Tryptophan | + | 18.7 a |
| 240R | + | 14.3 cd |
| 308R* + Tryptophan | + | 13.9 de |
| 389R | + | 13.6 de |
| 308R* | + | 13.6 de |
| 380R | + | 12.9 ef |
| 276R | + | 12.9 ef |
| 268R* | + | 12.9 ef |
| 7SR7 | + | 11.9 fg |
| P767 | − | 11.9 fg |
| 299R | + | 11.8 gh |
| T565 | + | 10.7 i |
| Tryptophan | − | 10.2 i |
| P56 | − | 10.2 i |
| P1016 | − | 9.9 i |
| Control | − | 7.7 j |

EXAMPLE 4

Use of Bactericides

The effects of bactericides on fruit russetting of pear trees was investigated. Terramycin was applied every 3-5 days at a concentration of 100 μg/ml sprayed to run off. Various bacterial compositions were applied as before. The A526 and A506 strains set forth in Table 3 below are both oxidase-positive fluorescent pseudomonads, one being *P. fluorescens* and the other being *P. putida*. As before, the greatest percent russetting was seen when fruit was innoculated with IAA-producing bacteria. Application of terramycin alone reduced russetting over that seen for the positive control, but produced russetting greater than control levels. This may have been caused by repopulation with auxin-producing bacteria after the surface colonies were reduced. The results of this experiment are set forth in Table 3 below.

TABLE 3

Severity of Fruit Russetting on Pear Trees Treated with Antagonistic Bacteria and IAA-producing Bacterial Strains Marysville, California

| Treatment | IAA Production | Russetted Area (%) |
|---|---|---|
| TS65 + 308R + 380R | + | 6.04 a |
| Terramycin | − | 4.20 b |
| A526 + Terramycin | − | 4.18 b |
| A506 + Terramycin | − | 3.67 bc |
| A526 | − | 3.39 cd |
| Control | − | 3.20 cd |
| A506 | − | 2.81 d |

EXAMPLE 5

Fruit Russetting on Pears Treated With Bactericides or Antagonistic Bacteria Pears were treated with various bactericides or antagonistic bacteria and the percent russetting measured. The results are set forth in Table 4 below. The microorganism strains have been previously identified. Kocide 101 contains cupric hydroxide and is known to sometimes increase russetting due to toxicity of the copper ions. Kocide 101 was applied at the rate of 1 lb. per 100 gallons. Phosphoric acid was applied twice, once about one week after flowering and again about two weeks later. The phosphoric acid treatment was intended to prevent frost injuries caused by bacterial ice nuclei. Bactericides were applied at a rate of 100 ppm weekly for seven weeks following flowering. Chlorox (0.2%) was applied 30 min before bacteria to reduce native bacteria (once at flowering). Chlorox apparently was somewhat toxic to developing fruit. The results are similar to those seen above in Table 3.

TABLE 4

Severity of Fruit Russetting on Pear Treated with Bactericides or Antagonistic Bacteria Healdsburg, California

| Treatment | Fruit Russet % Russet | Lot % Russet |
|---|---|---|
| Kocide 101 | 5.29 | 0.72 a |
| Terramycin 200 ppm | 3.28 | 0.52 a |
| Streptomycin + B7 | 2.69 | 0.43 c |
| Streptomycin + A510 | 2.63 | 0.42 cd |
| Streptomycin + Terramycin + H₃PO₄ | 2.57 | 0.41 cd |
| A506 | 2.57 | 0.41 cd |
| Hyamine | 2.51 | 0.40 cd |
| Chlorox + A510 | 2.51 | 0.40 cd |
| Chlorox + B7 | 2.45 | 0.30 cde |
| Streptomycin control | 2.45 | 0.39 cde |
| Control | 2.40 | 0.38 cdef |
| H₃PO₄ | 2.34 | 0.37 cdefg |
| Chlorox + A506 | 2.29 | 0.36 cdefg |
| Streptomycin + A506 | 2.29 | 0.36 defg |
| B7 | 2.24 | 0.35 defgh |
| Streptomycin + A506 | 2.24 | 0.35 defgh |
| Chlorox + A526 | 2.24 | 0.35 defgh |
| A526 | 2.14 | 0.33 efgh |
| Chlorox control | 2.04 | 0.31 fgh |
| Thiourea | 2.00 | 0.30 gh |
| Streptomycin (200 ppm) + Terramycin (200 ppm) | 2.00 | 0.30 gh |

EXAMPLE 6

Pear Fruit Russetting

An additional experiment was carried out in a manner as described in Example 5. The results are set forth in the following table.

TABLE 5

Severity of Pear Fruit Russetting on Trees Treated with Bactericides and Antagonist Bacteria

| Treatment | Fruit Russet Index |
|---|---|
| Control | 3.46 a |
| Kocide 101 | 3.34 a |
| Streptomycin + Terramycin | 2.60 b |
| A526 | 2.44 c |
| A506 | 2.15 d |
| F (treatment) | 129.02 |
| LSD 5% | 0.13 |

EXAMPLE 7

Pear Fruit Russetting

An additional experiment was carried out in a manner as described in Example 5. The results are set forth in the following table.

TABLE 6

Severity of Pear Fruit Russetting on Trees Treated with Antagonistic Bacteria and Bactericides

| Treatment | Russet (% of Surface) |
|---|---|
| Chlorox + A506 | 12.44 a |
| Streptomycin + Terramycin + A526 | 12.35 a |
| Chlorox + A526 | 11.05 b |
| Control | 10.92 b |
| Chlorox | 10.54 bc |
| Streptomycin + Terramycin + A506 | 10.07 bcd |

TABLE 6-continued

Severity of Pear Fruit Russetting on Trees
Treated with Antagonistic Bacteria and Bactericides

| Treatment | Russet (% of Surface) |
|---|---|
| A506 | 9.91 bcd |
| Streptomycin + Terramycin | 9.46 cd |
| A526 | 9.02 d |

EXAMPLE 8

Pear Fruit Russetting

An additional experiment was carried out in a manner as described in Example 4. The results are set forth in the following table.

TABLE 7

Incidence of Pear Fruit Russetting from Orchards
Treated with Bactericides or Antagonistic Bacteria

| Treatment | Russet (Fraction of Fruit) |
|---|---|
| Streptomycin + Terramycin | 0.85 a |
| Control | 0.78 a |
| A506 | 0.61 b |
| A526 | 0.57 b |

EXAMPLE 9

Pear Fruit Russetting

As additional experiment was carried out in a manner as described in Example 5. The results are set forth in the following table.

TABLE 8

Severity of Pear Fruit Russetting on Trees Treated
with Antagonistic Bacteria and/or Bactericides

| Treatment | Russet (% of Surface) |
|---|---|
| A1105 | 6.15 a |
| Control | 6.11 a |
| Chlorox + A506 + A526 | 5.84 ab |
| A506 + A526 | 5.33 bc |
| P40* | 5.30 bc |
| Streptomycin + Terramycin | 5.24 c |

TABLE 8-continued

Severity of Pear Fruit Russetting on Trees Treated
with Antagonistic Bacteria and/or Bactericides

| Treatment | Russet (% of Surface) |
|---|---|
| Streptomycin + Terramycin + A506 + A526 | 3.34 d |

*The strain P40 is a *P. syringi* strain.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of reducing fruit russetting on growing fruit, which comprises:
   inoculating a surface of a stone or pome fruit or an open flower from which said fruit develops with an auxin-deficient pseudomonad bacteria in an amount sufficient to reduce the population of auxin-producing bacteria on said surface.

2. The method of claim 1, wherein said auxin-deficient bacteria are introduced by contacting auxin-deficient bacteria with said fruit during initial stages of fruit formation.

3. The method of claim 2, wherein said contacting occurs prior to petal drop.

4. The method of claim 1, wherein said auxin is indole-3-acetic acid.

5. The method of claim 1, wherein said auxin-deficient bacteria are introduced by contacting auxin-deficient bacteria with pistils when fruit flowers are open.

6. The method of claim 1, wherein said auxin-deficient bacteria are introduced by contacting auxin-deficient bacteria with the surface of said stone or pome fruit.

* * * * *